United States Patent
Agostinelli et al.

(10) Patent No.: US 10,194,295 B2
(45) Date of Patent: *Jan. 29, 2019

(54) SYSTEM AND METHOD FOR SMART MATERIAL MONITORING

(71) Applicant: IdeaCuria Inc., Richmond Hill (CA)

(72) Inventors: Gregory A. Agostinelli, Richmond Hill (CA); Steven Nashed Hanna, Richmond Hill (CA); Ionut Alexandru Mirel, North York (CA)

(73) Assignee: IDEACURIA INC., Richmond Hill (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/940,052

(22) Filed: Mar. 29, 2018

(65) Prior Publication Data
US 2018/0227730 A1  Aug. 9, 2018

Related U.S. Application Data

(63) Continuation of application No. 15/179,368, filed on Jun. 10, 2016, now Pat. No. 9,967,696.

(60) Provisional application No. 62/174,918, filed on Jun. 12, 2015.

(51) Int. Cl.
| | |
|---|---|
| *H04W 4/70* | (2018.01) |
| *G01N 27/02* | (2006.01) |
| *G01N 33/14* | (2006.01) |
| *G08C 17/02* | (2006.01) |
| *G01N 21/31* | (2006.01) |
| *G01K 1/02* | (2006.01) |
| *H04L 29/08* | (2006.01) |

(52) U.S. Cl.
CPC .............. *H04W 4/70* (2018.02); *G01N 27/02* (2013.01); *G01N 33/146* (2013.01); *G08C 17/02* (2013.01); *G01K 1/022* (2013.01); *G01N 21/31* (2013.01); *H04L 67/12* (2013.01)

(58) Field of Classification Search
CPC ....... H04W 4/70; G01N 27/02; G01N 33/146; G01N 21/31; G08C 17/02; H04L 67/12; G01K 1/022
See application file for complete search history.

(56) References Cited

U.S. PATENT DOCUMENTS

| | | | | |
|---|---|---|---|---|
| 9,285,331 | B2* | 3/2016 | Minteer | .................. B01L 3/502 |
| 2006/0009865 | A1* | 1/2006 | Goldfine | ................ G05D 23/26 |
| | | | | 700/29 |
| 2009/0026090 | A1* | 1/2009 | Danyluk | ................ G01N 27/02 |
| | | | | 205/775 |
| 2015/0285752 | A1* | 10/2015 | Kozicki | ............. A01D 41/1243 |
| | | | | 324/649 |

* cited by examiner

*Primary Examiner* — Mohamed Barakat
(74) *Attorney, Agent, or Firm* — Perry + Currier Inc.

(57) ABSTRACT

A system for monitoring the characteristics of a material by measuring electrical properties of a material uses a material monitoring device and a cloud database that relates electrical properties of a material to characteristics of that material. The aging and fermentation processes of wine and other alcohols can be monitored. The status and decomposition of foodstuffs can be monitored. The progress of chemical reactions in a vessel can be monitored. Water quality of water from a water conduit can be monitored. These characteristics can be indicated on a product monitoring device or can be communicated to an external computing device.

15 Claims, 7 Drawing Sheets

SYSTEM AND METHOD FOR SMART MATERIAL MONITORING

CROSS-REFERENCE TO RELATED APPLICATIONS

This application is a continuation application of U.S. patent application Ser. No. 15/179,368, file Jun. 10, 2016, which claims priority to U.S. 62/174,918, filed Jun. 12, 2015, all of which are incorporated herein by reference.

FIELD

The present invention relates generally to material monitoring. More particularly, the present invention relates to a system and method for monitoring characteristics of a material via the electrical properties of the material.

BACKGROUND

There are many products sold today comprising materials that have characteristics that change over time, have the potential to expire, or may be contaminated. Consumers generally do not have a reliable means of monitoring the current status and characteristics of these products before or after purchasing or delivery. One class of such products is beverages, especially wines, which are known to change characteristics over time. Another class of such products is foodstuffs. A common problem with beverage and foodstuff products is that these products may spoil, decompose, or proceed past their ideal period for consumption, maturity point, or peak flavor point. A further class is water that can be delivered by plumbing or water bottles. Potential problems with water include contamination, which may affect taste or even health.

For beverage products and foodstuffs, some manufacturers provide an estimated "best before" date or a date on which the product was produced, which serves as a crude benchmark for estimating when a product has spoiled or passed its ideal consumption point. The typical consumer relying on these dates, however, must trust that the product contained within the packaging is still in good condition upon consumption and that it will match the characteristics advertised by the manufacturer.

Another class of materials that experiences relevant changes in characteristics over time are chemical products. The changes may be induced by environmental factors or they may occur spontaneously. They may be due to physical process changes such as evaporation or on-going chemical reaction processes such as ion exchange or other reactions. A chemical substance may only be useful to the purchaser when it possesses characteristics within a particular range.

Current solutions to monitoring beverages, foodstuffs, and similar materials typically involve invasive testing of the product or measurements performed on gas/vapor given off by the product. Many solutions require that the container be opened, thus altering the product's state or in many cases accelerating the spoiling process. Further, solutions that reference the gas/vapor given off by the product are indirect and may have reduced accuracy or may be incapable of measuring the desired characteristics.

SUMMARY

It is an object of the present invention to provide a novel system and method for monitoring characteristics of a material which obviates or mitigates at least one disadvantage of the prior art.

Accordingly, it is desired to have a system and method for monitoring a material by non-invasively performing measurements on the material and transmitting these measurement data to external computing devices for storage, computation, monitoring, and determination of characteristics of the material.

According to an aspect of the specification, a system for monitoring characteristics of a material is provided. The system includes a vessel defining an interior for containing the material, the vessel further defining an opening in communication with the interior; a stopper with an exterior end oriented away from the interior of the vessel and an interior end oriented toward the interior of the vessel, the stopper disposed within the opening of the vessel, the stopper comprising: a sensor device situated at the interior end of the stopper, the sensor device comprising an input electrode and an output electrode, the input and output electrodes being configured to measure an electrical property of the material; a communication device configured to transmit measurement data corresponding to the measured electrical property of the material; an electrical circuit connected to the sensor device and the communication device; a power source for powering the sensor device, communication device, and electrical circuit; and a stopper body housing the sensor device, the communication device, and the electrical circuit, the stopper body being shaped and sized for preventing material leakage from the vessel; and an external computing device remote from the vessel, the external computing device configured for data communication with the communication device of the stopper, the external computing device comprising a database comprising library data relating one or more measured electrical properties of the material to characteristics of the material.

According to another aspect of the specification, a system for monitoring characteristics of a material is provided. The system includes a sensor device, the sensor device comprising an input electrode and an output electrode, the input and output electrodes being configured to contact the material to measure at least one electrical property of the material; a communication device configured to transmit measurement data corresponding to the measured electrical properties of the material; an electrical circuit connected to the sensor device and the communication device; a power source for powering the sensor device, communication device, and electrical circuit; and a body, the body comprising an interior end and an exterior end, the body housing the sensor device, the communication device, and the electrical circuit, the sensor device situated at the interior end of the body.

According to another aspect of the specification, a method for monitoring the characteristics of a material is provided. The method includes measuring an electrical property of the material using a pair of electrodes; transmitting to an external computing device remote from the pair of electrodes measurement data corresponding to a measured electrical property of the material; comparing the measurement data of the measured electrical property to library data at the external computing device, the library data relating the electrical property of the material to characteristics of the material; and determining a characteristic of the material based on the comparison of the measured electrical property to the library data.

Other features and advantages of the present invention are described more fully below.

BRIEF DESCRIPTION OF THE DRAWINGS

Preferred embodiments of the present invention will now be described, by way of example only, with reference to the attached Figures, wherein.

DETAILED DESCRIPTION

The invention relates to a method and system for monitoring characteristics of a material via the electrical properties of the material. The system includes a material monitoring device for taking electrical measurements of the material, and includes an external cloud computing device containing a database with library data which relates electrical measurements of a material to characteristics of that material. For example, the measured electrical impedance of wine may be related to state of the wine throughout its aging process.

The material monitoring device can be made sufficiently compact to be able to directly take measurements inside small vessels containing materials, such as wine bottles containing wine, or can be made sufficiently compact to be able to directly take measurements along small conduits transporting a material, such as a water faucet or water meter transporting water. Additionally, the material monitoring device can be made with electrodes that can be in direct contact with the material being monitored, improving the electrical connection with the material and thereby the accuracy of any electrical measurement taken, without disturbing the material by requiring the vessel to be opened for inspection. Furthermore, the material monitoring device can be made with minimal storage and processing capabilities, with storage and processing duties being handled by an external cloud computing device, allowing for efficient energy operation of the material monitoring device.

A library relating electrical measurements of materials to characteristics of those materials can enable a model for determining characteristics of a material to be trained by machine learning techniques. The system can contribute measurement data to the library data thereby training a machine learning model to recognize relationships between electrical properties of materials and characteristics of those materials. For example, by the application of machine learning techniques, it may become recognized that the measured electrical impedance of wine may be related to state of the wine throughout its aging process.

Figure 1:
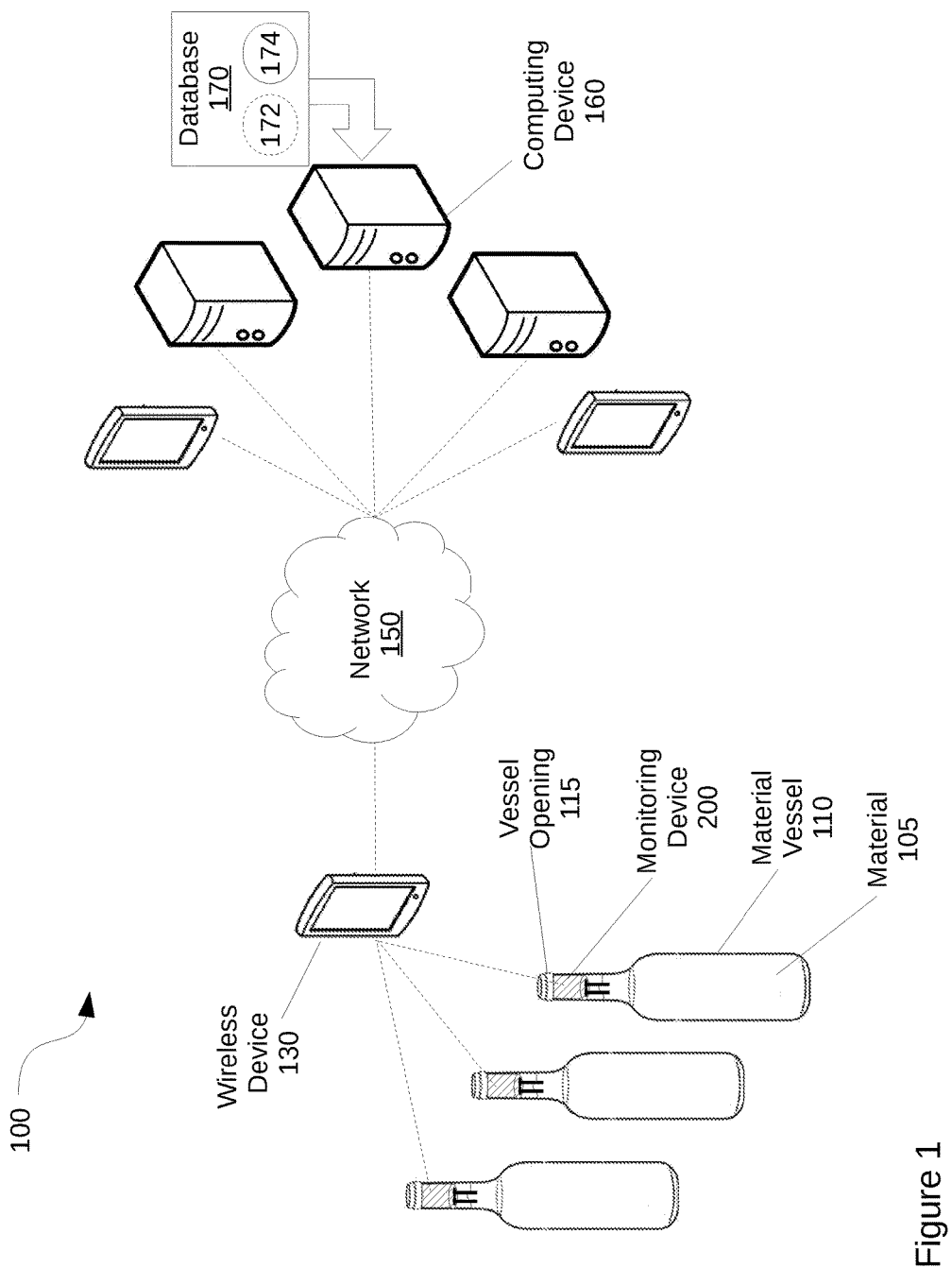
FIG. 1 depicts a schematic diagram of a system for monitoring characteristics of a material, according to a non-limiting embodiment.

FIG. 1 shows a system 100 for monitoring a material 105, according to a non-limiting embodiment of the present invention. The system 100 comprises a material vessel 110 defining a material vessel opening 115, a material monitoring device 200, a wireless device 130, a network 150, and one or more computing devices 160 storing a database 170. The vessel 110 contains material 105 to be monitored. The database 170 stores measurement data 172 and library data 174. The material monitoring device 200 communicates with the wireless device 130, and the wireless device 130 in turn communicates with the computing device 160 via one or more computer networks, shown as network 150, which can include a wireless cellular data network, a Wi-Fi network, a local-area network, a wide-area network (WAN), a Bluetooth pairing or connection, the internet, a virtual private network (VPN), a combination of such, and similar.

In this description, the material 105 will be considered to be wine, and the material vessel 110 will be considered to be a wine bottle. Wine in a wine bottle is merely one example, however, and the invention is not limited to monitoring a particular class of materials, whether the material is a fluid, liquid, gas, solid, beverage, foodstuff, chemical, and the vessel is not limited to a particular class of vessel. In addition, other types of containers and delivery conduits instead of vessels are contemplated, such as cartons, packages, kegs, water pipes, water bottles (e.g., office-style water coolers), to name a few.

In the present embodiment, the material monitoring device 200 comprises a wine bottle cork which houses one or more sensors and a communication device, as discussed in greater detail below. Briefly, the material monitoring device 200 measures electrical properties of the wine and transmits the results, and optionally along with other ancillary data, to the wireless device 130. It is contemplated that, in other embodiments, the system 100 includes a plurality of material monitoring devices 200 monitoring a plurality of materials 105. An advantage of housing the material monitoring device 200 within a wine bottle cork is that the wine bottle need not be opened, and thus disturbed, in order to inspect the wine for a characteristic.

The wireless device 130 is in communication with the computing device 160 which stores the database 170. Measurement data is periodically transmitted by the material monitoring device 200 to the wireless device 130, which in turn transmits the measurement data to the computing device 160 and is indicated as measurement data 172. The library data 174 stores existing data relating one or more electrical properties of a material 105, in this case wine, to characteristics of the material 105. In other embodiments, the system 100 includes a plurality of wireless devices 130, each in communication with one or more material monitoring device 200.

The computing device 160 is configured to compute, correlate, or otherwise determine a characteristic of the material 105 by comparing the measured electrical properties of the material 105 in measured data 172 to library data 174. The computing device 160 can communicate an indication of this characteristic or the characteristic itself to interested parties, such as a consumer, owner, retailer, or manufacturer across the network 150, whether through the wireless device 130 or otherwise. An indication that a characteristic has reached a threshold can be transmitted as an alert to the wireless device 130. In other embodiments, the system 100 includes a plurality of computing devices 160 on a cloud computing network, in communication with one or more wireless devices 130.

The material monitoring device 200 takes measurements of the material 105 over lengths of time for prolonged periods of monitoring. In the present embodiment of monitoring the characteristics of wine, the system 100 could be used to monitor whether the wine is within the optimal taste window or outside of the optimal taste window.

In other embodiments, wine undergoing a fermentation process in a barrel is monitored via a material monitoring device 200 embedded within the bung of the barrel, or in another suitable location, for indicating the level of completion of the fermentation cycle. Additionally, the aging process of wine can be monitored, with an alert being sent to the wireless device 130 to indicate that the wine has completed its aging process and it is ready to ship to market. Additional characteristics of wine that could be monitored, whether in a bottle or aging in a barrel, include sweetness of flavor, acidity, tannin, fruitiness of flavor, body, aroma, or any other suitable characteristic of wine that is usually measured. These characteristics, although not measurable directly, can be inferred from comparing measurement data 172 to library data 174, which relates electrical properties of wines to known characteristics of wines.

In the present embodiment, the wireless device 130 includes a smart phone running an operating system such as, for example, Android®, iOS®, Windows® mobile, BB 10, or similar. The wireless device 130 receives alerts and indications from the computing device 160 regarding characteristics of a material being monitored, thereby serving as an end-user device for monitoring a material.

In other embodiments, the wireless device 130 includes a tablet computer, a personal digital assistant (PDA), computer, or other machine with communications ability within range of the material monitoring device 200. In these embodiments, the wireless device 130 similarly serves as an end-user device for monitoring a material.

In still other embodiments, the wireless device 130 includes a wireless access point, wireless router, or similar network device. In these embodiments, a computing device 160 serves as an end-user device for monitoring a material. In still other embodiments, a computing device 160 is in communication with a second computing device 160, the second computing device 160 serving as an end-user device for monitoring a material.

In the present embodiment, a computing device 160 includes a computing device running a server application with storage, communication, and processing means.

A person skilled in the art upon reading this specification will appreciate that the wireless device 130 and the cloud computing device 160 can each be more generally referred to as external computing devices, and that in certain embodiments the responsibility of each external computing device may be interchangeable. In the present embodiment, measurement data 172 is transmitted from the material monitoring device 200, temporarily stored on the wireless device 130, and transmitted to a computing device 160 for permanent storage on database 170, for computation, and for determination of a characteristic of the material with reference to library data 174. In the present embodiment, cost, size, and energy use of the monitoring device 200 is reduced by keeping storage and computation away from the material monitoring device 200, and having only measurement and data transmission take place on the monitoring device 200, with a wireless device 130 acting as an intermediary data transport device.

In other embodiments, these responsibilities can be distributed arbitrarily across the monitoring device 200, wireless device 130, and computing device 160. For example, the database 170 comprising library data 174 may be stored on a single wireless device 130, or may be distributed across several wireless devices 130, eliminating the need for a computing device 160. Alternatively, a material monitoring device 200 or a plurality of material monitoring devices 200 may be in direct communication with a computing device 160 or a plurality of computing devices 160, eliminating the need for a wireless device 130. Furthermore, the person skilled in the art upon reading this specification will appreciate that storage, computation, correlation, and machine learning techniques can take place directly on a single or a plurality of material monitoring devices 200, on a single or plurality of wireless devices 130, or on a single or plurality of computing devices 160. In further embodiments, a plurality of material monitoring devices 200 include sufficient storage and communication capability to host a distributed database comprising library data, and sufficient processing capability to determine characteristics of materials and communicate alerts of such characteristics.

Figure 2:
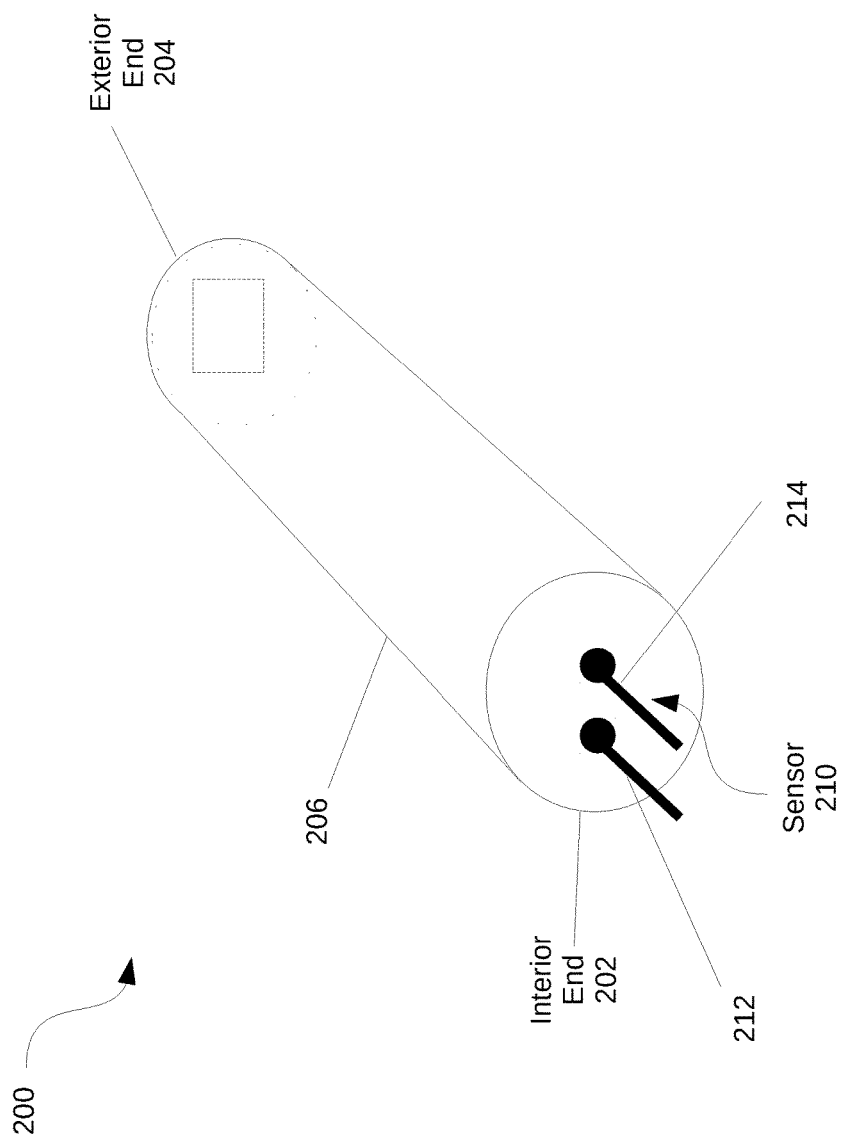
FIG. 2 depicts a perspective view of a device for monitoring characteristics of a material, according to a non-limiting embodiment.

In other embodiments, materials other than wine are monitored. For example, it is understood that the materials 105 being monitored can comprise fluids, liquids, gases, solids, plasmas, beverages, other alcohols, foodstuffs, chemicals, chemicals undergoing chemical reactions, or any other suitable material of interest for which electronic monitoring would be feasible. Other examples include medical vaccine monitoring, medication monitoring, or medication authentication. Furthermore, the material vessels 110 includes wine bottles, wine barrels, bottles or barrels of other alcohols, casks, or beverage containers of any kind which can fit a material monitoring device 200. FIG. 2 depicts a perspective view of a material monitoring device 200 viewed from its interior end, according to a non-limiting embodiment. The material monitoring device 200 comprises an interior end 202, an exterior end 204, a body 206, and a sensor device 210, further comprising an output electrode 212 and an input electrode 214. With reference to the embodiment in FIG. 1, the material monitoring device 200 comprises a wine bottle cork with a sensor device located at its interior end 202.

In the present embodiment of a system for monitoring characteristics of wine in a wine bottle, when disposed within the opening of a wine bottle, the interior end 202 of the material monitoring device 200 is oriented toward the wine, with the sensor device 210 protruding from the interior end 202, and with output electrode 212 and input electrode 214 extending into the wine contained within the wine bottle.

However, in other embodiments for monitoring wine or other liquids, the output electrode 212 and input electrode 214 need not extend into the liquid, but rather conducts measurements on the gas/vapor in the headspace above the liquid to infer properties of the liquid, or is used to directly conduct measurements on a gas contained within the vessel.

In the present embodiment of a system for monitoring characteristics of wine in a wine bottle, the output electrode 212 is used to apply an electrical stimulus to the wine. In turn, the input electrode 214 is used to measure the response of the material to the electrical stimulus. The output electrode 212 and input electrode 214 comprises any suitable material for electrical conductivity, including gold, a gold-plated metal, platinum, a platinum-plated metal, carbon, graphite, graphene, silver, silver chloride, silicon, germanium, tin, iron, copper, or brass, or other suitable materials.

The body 206 is sized to plug the opening 115 of the material vessel 110. In the present embodiment for monitoring wine in a wine bottle, the body 206 comprises a wine bottle cork sized to plug the opening 115 of the wine bottle. However, in other embodiments, the body 206 comprises a barrel bung, a cap, a lid, or an attachment embedded into the side of a vessel, or any other means for housing a material monitoring device 200 with a sensor device 210 in contact with the material 105 being monitored. The material of the body 206 comprises any material suitable for the particular application, such as plastic, natural cork, synthetic cork, agglomerated cork, or wax for the wine bottle application.

Figure 3:
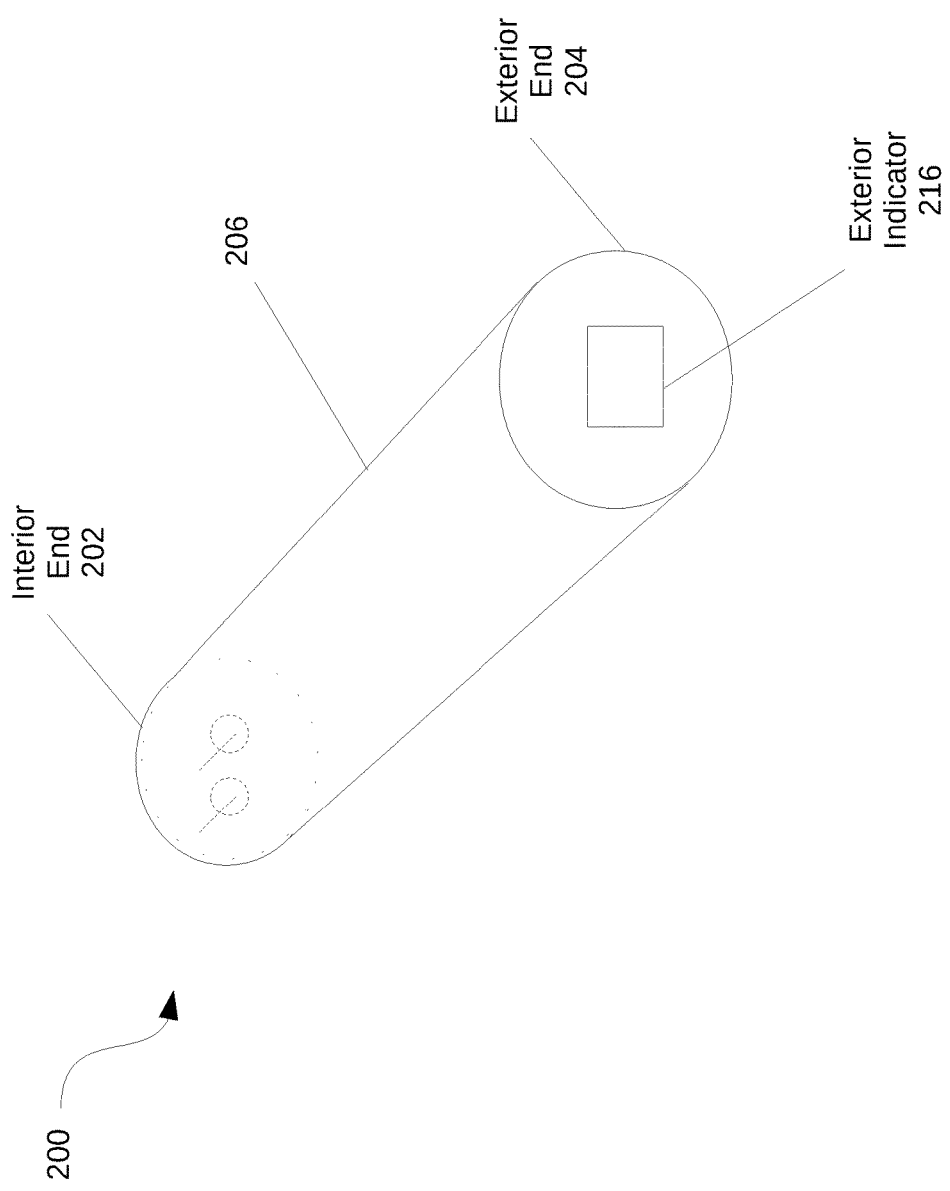
FIG. 3 depicts another perspective view of the device.

FIG. 3 depicts a perspective view of a material monitoring device 200 viewed from its exterior end 204. In the present embodiment, the material monitoring device 200 further comprises an exterior indicator 216 located at its exterior end 204 that indicates information regarding the status or characteristics of the material 105 being monitored.

The exterior indicator 2016 includes at least one of: a simple single color light-emitting diode (LED), a multi-color LED, a moving coil galvanometer, voltmeter or current meter, a piezoelectric transducer, a speaker, a buzzer, a siren, a relay switch, an optical bar graph, a counter such as a numerical counter or any suitable counter, liquid crystal display (LCD), or any other suitable indicator device that interfaces with the circuitry of the material monitoring device 200, as described in greater detail below.

In the present embodiment of a system for monitoring characteristics of wine in a wine bottle, the external indicator 216 comprises a three color LED, where the color red indicates the wine has passed its optimal point of consumption, the color yellow indicates the wine approaching the end of its optimal point of consumption, and the green colour indicates that the wine is within its optimal point of consumption.

Various embodiments of the material monitoring device 200 are contemplated. In one embodiment, the sensor device 210 includes a third electrode. In such an embodiment, the three electrodes are a working electrode, a reference electrode, and a counter electrode, thus enabling additional electro-analytical techniques. For example, the sensor device 210 includes a three-electrode potentiostat system for measuring redox reactions or other types of reactions.

In a further embodiment, the sensor device 210 includes only a single electrode. In such an embodiment, the sensor device 210 comprises no output electrode, but only a single input electrode for taking input measurements.

In some embodiments, the sensor device 210 includes two electrodes, with one input electrode providing electrical stimulus, and one return-path electrode for completing the electrical connection allowing a return electrical signal to return from the material being monitored.

In a further embodiment, the sensor device 210 includes a plurality of electrodes for providing stimulus to the material being monitored and/or for performing measurements.

In a further embodiment, the sensor device 210 includes a single electrode for performing measurements and/or providing a stimulus to the material being monitored and measuring the response on the material being monitored.

In further variations of the material monitoring device 200, the external indicator 216 may be omitted. In this variation, the status or characteristics of the material 105 may be communicated to and presented at wireless device 130 or cloud computing device 160.

Figure 4:
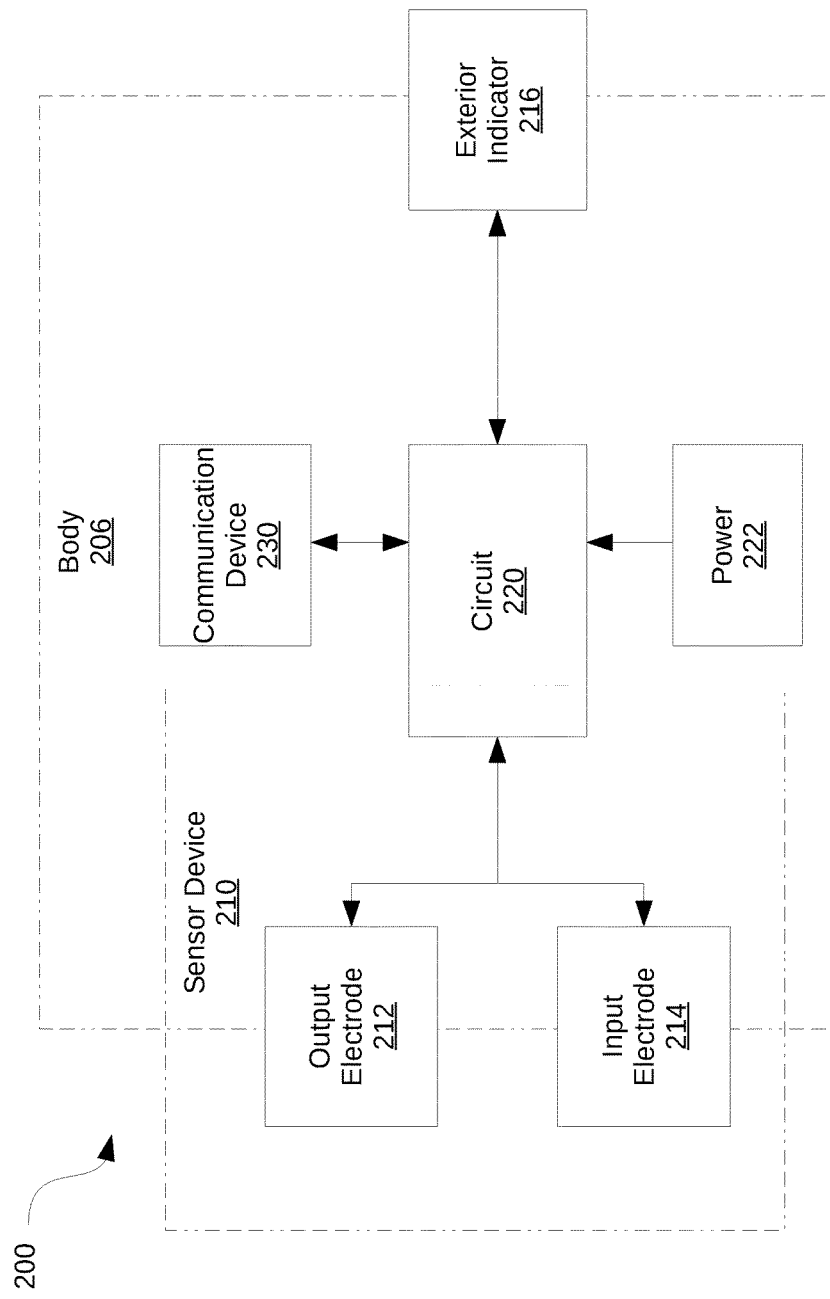
FIG. 4 depicts a functional block diagram of the device.

FIG. 4 depicts functional blocks of the material monitoring device 200, according to a non-limiting embodiment. The material monitoring device 200 comprises a sensor device 210 comprising an output electrode 212 and an input electrode 214. The material monitoring device 200 further comprises an exterior indicator 216, a communication device 230, power supply 222, and circuit 220.

The communication device 230 is configured to transmit data corresponding to measured electrical properties of the material 105 to the wireless device 130 and/or the cloud computing device 160, as the case may be. The communication device 230 comprises a communications antenna, or any other suitable communication device configurable to communicate directly with a wireless device 130.

The power supply 222 supplies power to the components of the material monitoring device 200. In the present embodiment, the power supply 222 comprises a power harvesting circuit. The power harvesting circuit harvests electrical power from the communications field or by any other suitable means. In other embodiments, the power supply 222 comprises a battery, a solar cell, or external power supply connection, such as an AC or DC connection. Although in the present embodiment the power supply 222 is illustrated as being housed within the body 206 of the material monitoring device 200, in other embodiments it is contemplated that the power supply could be exterior to the body 206.

The circuit 220 comprises circuitry for providing electrical connections between the sensor device 210, communication device 230, power supply 222, and exterior indicator 216. In various embodiments, a portion of the circuit 220 forms part of the sensor device 210. Furthermore, in some embodiments, the circuit 220 includes one or more of the following: a processor, a microcontroller, a state machine, a logic gate array, an application-specific integrated circuit (ASIC), a system-on-a-chip (SOC), a field-programmable gate array (FPGA), or similar, capable of executing, whether by software, hardware, firmware, or a combination of such, a method for monitoring characteristics of a material as discussed in greater detail below. In the present embodiment, the circuit 220 implements a system-on-a-chip (SOC). In some embodiments, the circuit 220 includes memory, where measurement data 172 is to be stored on the material monitoring device 200, before, or in addition to, being transmitted to the wireless device 130 or cloud computing device 160.

In various embodiments, the circuit 220 is a discrete electrical circuit made up of separate discrete electrical components. In other embodiments, the circuit 220 includes an ASIC, an FPGA, an SOC, or combinations thereof. Embodiments of the circuit 220 that include a combination of separate discrete electrical components and an ASIC, FPGA, and/or SOC are also contemplated. In various embodiments, portions of the circuit 220 that describe a logical state-machine are implemented as software and/or firmware that operate on a processor or microcontroller. In various embodiments, the circuit 220 further includes an electrode interface portion that includes circuit elements specific to the electrodes for performing electrical stimulation and electrical measurements, and such circuit elements can be considered to be part of the sensor device 210.

The material monitoring device 200 is configured to conduct electrical measurements of the material 105. In the present embodiment, the material monitoring device 200 conducts impedance spectroscopy, also known as dielectric spectroscopy, for electrically stimulating the material 105 and performing a measurement on the material 105. It is to be understood, however, that in other embodiments, other electro-analytical methodologies can be performed, such as potentiometry, coulometry, voltammetry, square wave voltammetry, stair-case voltammetry, cyclic voltammetry, alternating current voltammetry, amperometry, pulsed amperometry, galvanometry, and polarography, and other suitable electro-analytical methodologies. In various embodiments, several of the aforementioned methodologies are used in combination.

In other embodiments, the product monitoring device 200 comprises a sensor capable of taking additional measurements, such as acceleration, position, temperature, pressure, color, light intensity, light phase, density, surface tension, viscosity, resistance, impedance, voltage, current, charge, quantity of mass, quantity and direction of force, quantum mechanical properties, or any other suitable property that can be measured by a sensor. In yet other embodiments, the sensor includes a gyroscope or magnetometer.

In other embodiments, the product monitoring device 200 comprises a sensor with a digital interface designed to perform similar measurements, with the sensor interfacing with the circuit 220 through methods such as Two Wire Interface (TWI or I2C compatible), SPI interface, Microwire, 1-Wire, Single Wire Protocol (SWP), or any other suitable digital or analog communications methodologies.

The circuit 220 may control operations of the material monitoring device 200, including initializing the circuit 220 with required startup parameters, initiating and recording measurements of the sensor device 210, packetizing the measurement data 172 into data packets, controlling the communication device 230 for the reception and transmission of data, commands, and ancillary information, any firmware or software updates, and any other suitable information being transmitted or received.

Figure 5:
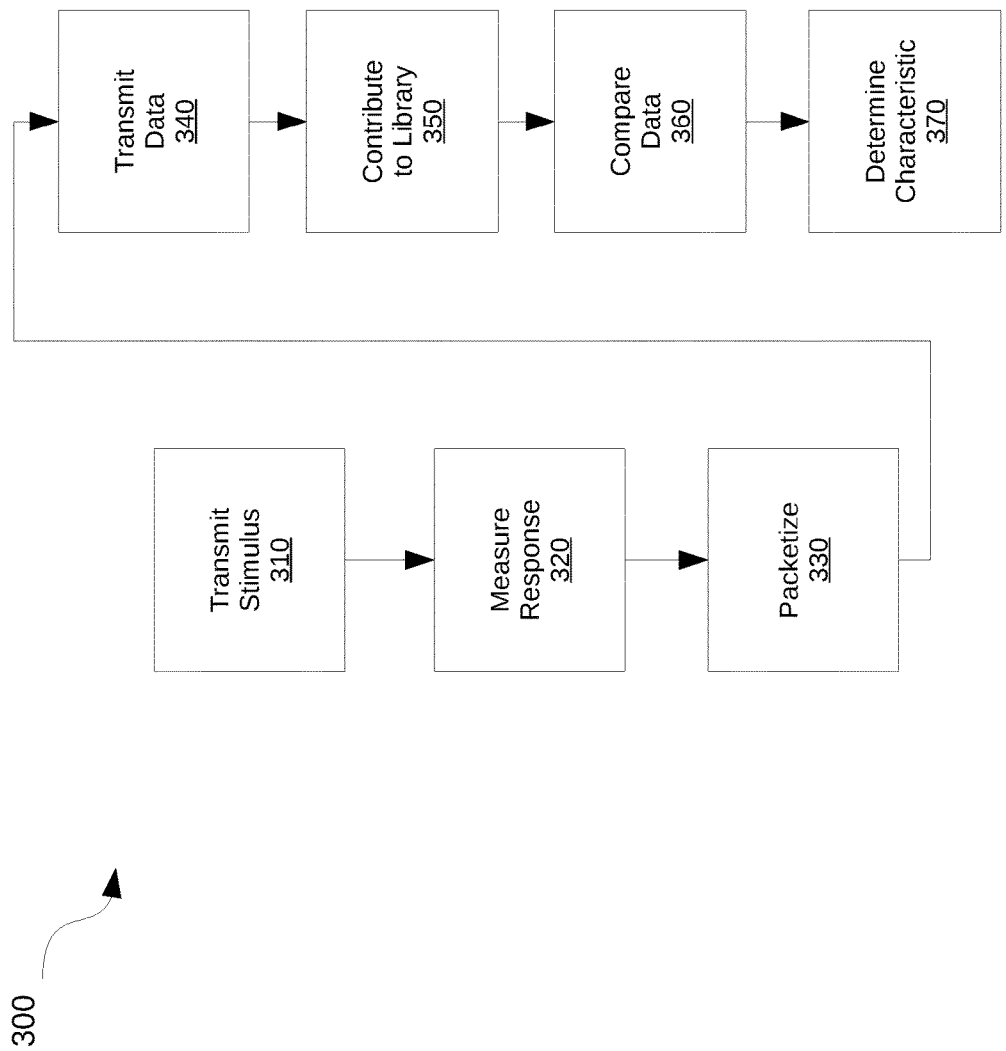
FIG. 5 depicts a flowchart of a method for determining a characteristic of a material, according to a non-limiting embodiment.

FIG. 5 depicts a flowchart of a method 300 for determining a characteristic of a material, according to a non-limiting embodiment. The method 300 is one way in which the characteristics of a material can be monitored. It is to be emphasized, however, that the blocks of method 300 need not be performed in the exact sequence as shown. The method 300 is described as performed by a system and device discussed herein, but this is not limiting and the method can alternatively be performed by other systems and/or devices. At block 310, an electrical stimulus is transmitted by output electrode 212 into material 105.

At block 320, a stimulus response of the material 105 to the electrical stimulus is measured by the input electrode 214.

At block 330, the measurement data 172 is packetized for transmission to an external computing device. In embodiments in which the circuit 220 comprises memory, the measurement data 172 is recorded on memory before transmission.

At block 340, measurement data 172 corresponding to a measured electrical property is transmitted by the communication device 230 to the wireless device 130, which in turn transmits the measurement data 172 to the computing device 160, which stores the measurement data 172 on database 170.

At block 350, in the present embodiment, the measurement data 172 transmitted at block 340 is contributed to the library data 174 in database 170. In other embodiments in which the measurement data 172 is not contributed to the library data 174, this block is omitted.

At block 360, measurement data 172 is compared to library data 174.

At block 370, a characteristic of the material 105 is determined based on the comparison of measurement data 172 to library data 174.

By application of method 300, a characteristic of a material 105 being monitored is determined with reference to the electrical properties of the material 105 and the library data 174. These characteristics, although not measurable directly, are inferred from comparing measurement data 172 to library data 174, which relates electrical properties of a material to known characteristics of materials. Furthermore, by application of method 300, a library relating electrical property data to material characteristic data is developed.

In various embodiments, machine learning techniques are applied. In one such embodiment, a neural network algorithm that employs a Bayesian algorithm and a decision tree analysis to classify the measurement data 172 and report the classified result in order to classify the characteristics of the material 105.

In another embodiment, canonical correlation is used on the measurement data 172 to report on the status of the material 105, including, in the case of monitoring the characteristics of wine, whether the wine is within the wine's optimal taste window or approaching its expiry point, and an estimate of how much time may be left before the wine is expected to reach its expiry point.

In another embodiment, a polynomial regression is used on the measurement data 172 to report on the status of the material 105 and also classify its characteristics.

In another embodiment, principal component analysis (PCA) is used on the measurement data 172 to report on the status of the material 105 and also classify its characteristics.

In another embodiment, principal component regression (PCR) is used on the measurement data 172 to report on the status of the material 105 and also classify its characteristics.

In other embodiments, other suitable data analysis techniques may be used, such as clustering analysis, correlation, neural network machine learning algorithms, support vector machine algorithms, random forest algorithms, or other appropriate algorithms.

In some embodiments, the material monitoring device 200 conducts measurements at regular intervals, as some applications require a delay time in order to perform a suitable measurement. In one such embodiment, the wireless device 130 sends instructions to material monitoring device 200 to conduct a measurement at an interval. In another such embodiment, the computing device 160 sends instructions to material monitoring device 200 to conduct a measurement at an interval.

In various embodiments where the material monitoring device 200 comprises a single electrode, blocks 310 and 320 are replaced with a block at which a measurement is taken. In various embodiments, where the material monitoring device 200 comprises one or more electrodes, modifications may be made to the method 300 by the person skilled in the art upon reading this specification as would be appropriate to conduct a desired measurement.

Figure 6:
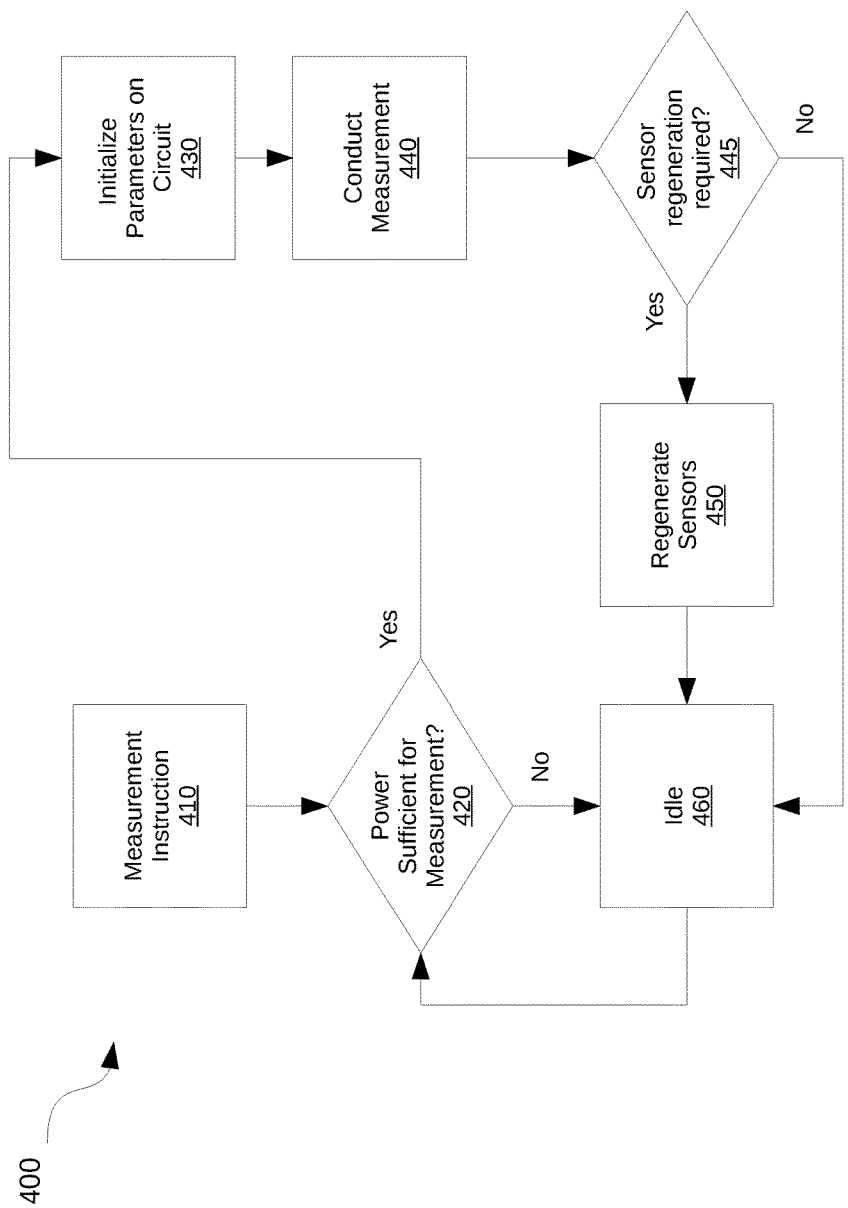
FIG. 6 depicts a flowchart of a method for initializing a device for monitoring characteristics of a material, according to a non-limiting embodiment.

FIG. 6 depicts a flowchart of a method 400 for initializing a material monitoring device 200, according to a non-limiting embodiment. The method 400 is one way in which the characteristics of a material can be monitored. It is to be emphasized, however, that the blocks of method 400 need not be performed in the exact sequence as shown. The method 400 is described as performed by a system and device discussed herein, but this is not limiting and the method can alternatively be performed by other systems and/or devices.

In the present embodiment, the material monitoring device 200 remains in an idle state with low energy consumption between conducting measurements. When instructed to conduct a measurement, the material monitoring device 200 undergoes a process of initialization to prepare to conduct a measurement. Upon concluding conducting a measurement, the material monitoring device 200 returns to an idle state.

At block 410, an instruction to conduct a measurement is received by the communication device 230 from an external computing device such as the wireless device 130 or computing device 160.

At block 420, it is determined whether the material monitoring device 200 has sufficient electrical power to conduct a measurement. If sufficient power is present, block 430 is executed. If sufficient power is not present, block 460 is executed. Whether sufficient electrical power is present may be determined by whether a suitable electrical connection is established with an outside power source, whether sufficient battery power is remaining, or whether the energy harvesting circuit has harvested sufficient power for operation.

At block 430, circuit parameters are initialized. For example, initialization includes initializing one or more parameters such as: processor or system clock frequency, analog circuit gain, analog circuit drive strength, analog circuit termination impedance, stimulation values, delay values, filter settings, and any other suitable programmable setting in the device. The aforementioned list of parameters is non-limiting and other parameters are contemplated.

At block 440, a measurement is conducted and compared to determine a characteristic of a material, as described with respect to method 300 in FIG. 5 above.

At block 445, it is determined whether sensor regeneration is required. If sensor regeneration is required, block 450 is executed. If sensor regeneration is not required, block 460 is executed. Some sensors 210 require a special regeneration cycle, and others do not, as will be apparent to the person skilled in the art upon reading this specification. For example, a three-electrode potentiostat measurement system that uses very sensitive electrodes may require a regeneration cycle to free ions from the electrode that may collect on the electrode during the measurement cycle.

At block 460, the material monitoring device 200 is in an idle state with low energy consumption. In the present embodiment where the power supply 222 is a power harvesting circuit, the material monitoring device 200 waits until sufficient power is harvested for a measurement to be conducted.

It will be understood by the person skilled in the art upon reading this specification that it is possible to add or omit blocks as necessary to execute any given measurement algorithm.

Figure 7:
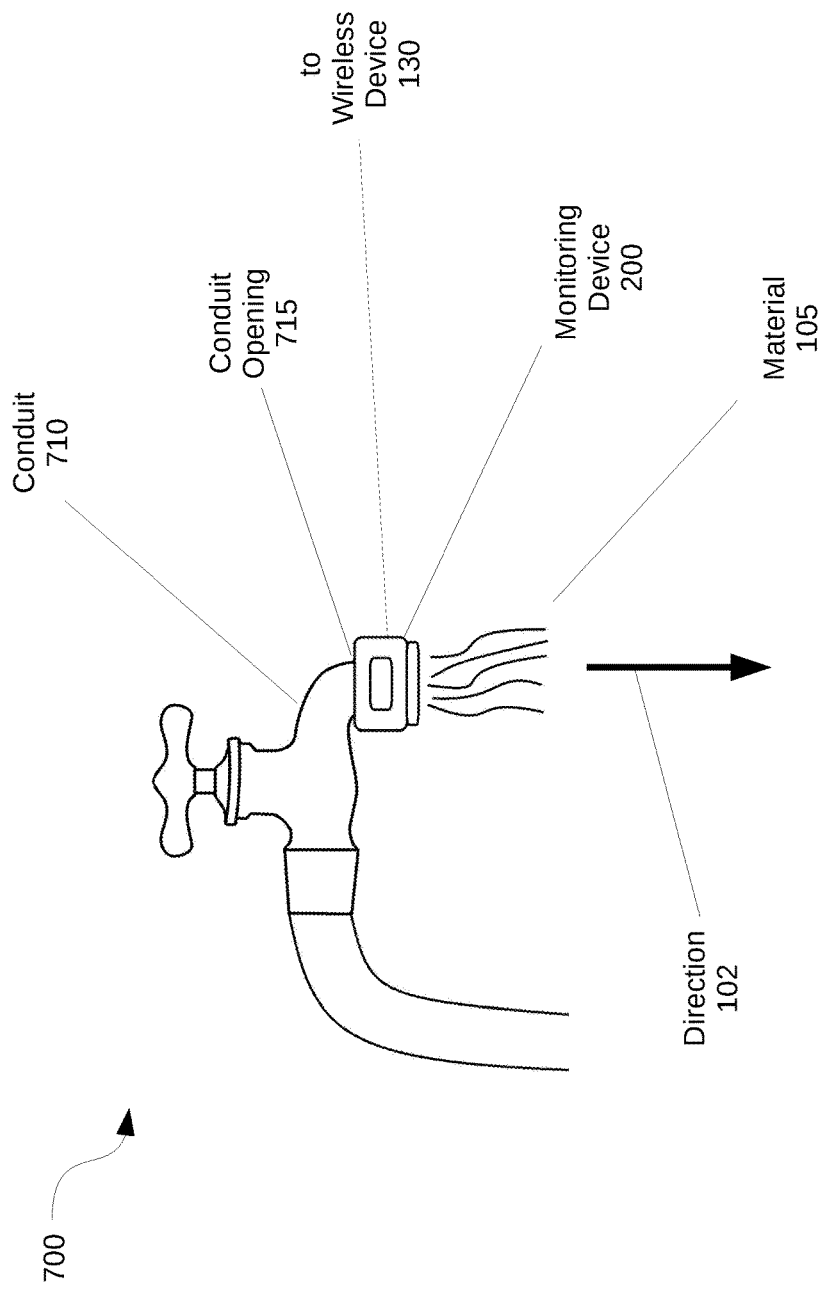
FIG. 7 depicts a schematic diagram of a system for monitoring characteristics of a material, according to a non-limiting embodiment.

In another application of the invention, FIG. 7 depicts a schematic diagram of a system 700 for monitoring characteristics of a material, according to a non-limiting embodiment. In system 700, a material 105 traveling in direction 102 passing through a conduit 710 is monitored by a material monitoring device 200 attachable to the conduit 710. The system 700 comprises other elements of system 100, including a wireless device 130, a network 150, a database 170, measurement data 172 and library data 174, and the above description may be referenced.

In the present embodiment, the material being monitored comprises tap water passing through a water conduit such as a water pipe or a water faucet. The material monitoring device 200 is located at the conduit opening 715 of the water pipe or water faucet.

In other embodiments, the material 105 includes beer, liquor, another beverage, a chemical, or any other fluid. In such embodiments, the conduit 710 comprises piping, tubing, hose, spout, or any other conduit suitable to transport the fluid.

In still other embodiments, the material 105 includes a solid foodstuff that is capable of flow through a conduit and is susceptible to electrical measurements from an electrode, such as, for example, granulated sugar. In such embodiments, the conduit 710 uses flowing air or gas, a conveyer, trough, or any other mechanism suitable to transport the solid. Another example of a solid or semi-solid foodstuff is tomato paste. Such a foodstuff may flow through a conduit and may be forced or extruded through a pair of electrodes that perform one or more of the electrical measurements described herein.

In some embodiments, the power supply 222 comprises a kinetic energy harvesting circuit capable of harvesting energy from the motion of the material 105.

It should be apparent from the above that characteristics of a material can be monitored via the electrical properties of the material by a low-power, compact, material monitoring device capable of direct yet non-invasive contact with a material, locatable within a vessel or conduit, in communication with a library of data for determining a characteristic of a material using an evolving model based on machine learning techniques. The scope of the claims should not be limited by the embodiments set forth in the above examples, but should be given the broadest interpretation consistent with the description as a whole.

What is claimed is:

1. A system for monitoring a characteristic of a material, the system comprising:
    a sensor device, the sensor device comprising an input electrode and an output electrode, the input and output electrodes being configured to contact the material to measure at least one signal relating to an electrical property of the material; and
    a processor in communication with the sensor device, the processor configured to apply machine learning for determining a not directly measurable characteristic of the material based on at least the at least one signal relating to an electrical property of the material, the machine learning applied via a machine learning model trained with library data to recognize the not directly measurable characteristic of the material, the library data relating previously measured signals relating to the electrical property of the material to known not directly measurable characteristics of the material.

2. The system of claim 1, further comprising:
    an electrical circuit;
    a communication device in communication with the sensor device via the electrical circuit and in communication with the processor via a network, the communication device configured to receive measurement data corresponding to the at least one signal from the sensor device and to transmit the measurement data to the processor via the network;
    a power source to power the sensor device, communication device, and electrical circuit; and
    a body to house the sensor device and the communication device.

3. The system of claim 2, wherein the body is attachable to a material conduit for transporting the material, the input and output electrodes of the sensor device extending into an interior of the material conduit.

4. The system of claim 3, wherein the material conduit comprises a water conduit.

5. The system of claim 2, wherein the body comprises a stopper configured to plug an opening of a vessel, the vessel defining an interior for containing the material, the input and output electrodes of the sensor device extending into an interior of the vessel.

6. The system of claim 5, wherein the vessel comprises a wine bottle, the material comprises wine, and the stopper comprises a wine bottle cork.

7. The system of claim 2, wherein the processor comprises an external computing device remote from the sensor device, the external computing device configured for data communication with the communication device, the external computing device comprising a database comprising library data relating one or more signals relating to electrical properties of the material to characteristics of the material.

8. The system of claim 7, wherein the library data corresponding to characteristics of the material comprises a characteristic selected from a group consisting of: optimal tasting window, age, fermentation status, flavor, acidity, tannin, fruitiness, body, aroma, and chemical reaction progress.

9. The system of claim 7, wherein the processor is further configured to contribute the at least one signal relating to an electrical property of the material and the determined not directly characteristic of the material to the database.

10. The system of claim 2, wherein the electrical circuit comprises an application-specific integrated circuit, another processor, a state machine, a field-programmable gate array, or a microcontroller.

11. The system of claim 2, wherein the power source is selected from a group consisting, of: a power harvesting circuit, a battery, a solar cell, and an alternating current electrical power adapter.

12. The system of claim 1, wherein one or more of the sensor device and the processor are configured to perform an analytical methodology selected from a group consisting of: potentiometry, coulometry, voltammetry, impedance spectroscopy, square wave voltammetry, stair-case voltammetry, cyclic voltammetry, alternating current voltammetry, amperometry, pulsed amperometry, galvanometry, and polarography.

13. The system of claim 1, wherein one or more of the sensor device and the processor are configured to perform an analytical methodology selected from a group consisting of: potentiometry, coulometry, voltammetry, impedance spectroscopy, square wave voltammetry, stair-case voltammetry, cyclic voltammetry, alternating current voltammetry, amperometry, pulsed amperometry, galvanometry, and polarography.

14. The system of claim 1, wherein the output electrode is configured to apply electrical stimulus to the material, and the input electrode is configured to measure a response to the electrical stimulus applied to the material.

15. The system of claim 1, wherein the material comprises a fluid, and wherein the input electrode and output electrode extend into the fluid.

* * * * *